(12) United States Patent
Otohata et al.

(10) Patent No.: US 11,563,237 B2
(45) Date of Patent: Jan. 24, 2023

(54) LITHIUM ION SECONDARY BATTERY INCLUDING POROUS INSULATING LAYER FORMED ON POSITIVE ELECTRODE AND ELECTROLYTE SOLUTION HAVING HALOGENATED CYCLIC ACID ANHYDRIDE

(71) Applicant: NEC Corporation, Tokyo (JP)

(72) Inventors: Makihiro Otohata, Tokyo (JP); Noboru Yoshida, Tokyo (JP)

(73) Assignee: NEC CORPORATION, Tokyo (JP)

( * ) Notice: Subject to any disclaimer, the term of this patent is extended or adjusted under 35 U.S.C. 154(b) by 121 days.

(21) Appl. No.: 16/608,008

(22) PCT Filed: Apr. 24, 2018

(86) PCT No.: PCT/JP2018/016566
§ 371 (c)(1),
(2) Date: Oct. 24, 2019

(87) PCT Pub. No.: WO2018/199072
PCT Pub. Date: Nov. 1, 2018

(65) Prior Publication Data
US 2020/0153044 A1    May 14, 2020

(30) Foreign Application Priority Data

Apr. 25, 2017  (JP) .............................. JP2017-086233

(51) Int. Cl.
*H01M 10/0567* (2010.01)
*C07D 305/10* (2006.01)
(Continued)

(52) U.S. Cl.
CPC ...... *H01M 10/0567* (2013.01); *C07D 305/10* (2013.01); *H01M 10/058* (2013.01); *H01M 10/0525* (2013.01); *H01M 2300/0025* (2013.01)

(58) Field of Classification Search
CPC ......... H01M 10/0567; H01M 10/0525; H01M 10/058
(Continued)

(56) References Cited

U.S. PATENT DOCUMENTS

2005/0053843 A1   3/2005  Takahashi
2007/0122715 A1*  5/2007  Fujino ................. H01M 10/052
                                               429/251
(Continued)

FOREIGN PATENT DOCUMENTS

CN       1595711 A       3/2005
CN     106104899 A      11/2016
(Continued)

OTHER PUBLICATIONS

Office Action dated Nov. 17, 2020 in Japanese Application No. 2019-514523.
(Continued)

*Primary Examiner* — Sean P Cullen
(74) *Attorney, Agent, or Firm* — Sughrue Mion, PLLC

(57) ABSTRACT

A purpose of the present invention is to provide a lithium ion secondary battery in which an increase in internal resistance is suppressed and a halogenated cyclic anhydride is used as an electrolyte additive. The lithium ion secondary battery according to the present invention comprises a positive electrode and an electrolyte solution, wherein a porous layer comprising an insulating filler is formed on the positive electrode, and the electrolyte solution comprises 0.005 to 10 weight % of a halogenated cyclic acid anhydride.

3 Claims, 2 Drawing Sheets

(51) Int. Cl.
*H01M 10/0525* (2010.01)
*H01M 10/058* (2010.01)

(58) Field of Classification Search
USPC .................................................. 429/329, 337
See application file for complete search history.

(56) References Cited

U.S. PATENT DOCUMENTS

| | | | | |
|---|---|---|---|---|
| 2008/0299461 | A1* | 12/2008 | Kim ...................... | H01M 10/02 |
| | | | | 429/245 |
| 2009/0286164 | A1* | 11/2009 | Wada .................... | H01M 4/525 |
| | | | | 429/338 |
| 2009/0311608 | A1 | 12/2009 | Hirose et al. | |
| 2012/0316716 | A1 | 12/2012 | Odani et al. | |
| 2016/0226098 | A1 | 8/2016 | Yoshida et al. | |
| 2016/0351957 | A1* | 12/2016 | Taeda ..................... | H01G 11/64 |
| 2017/0077552 | A1* | 3/2017 | Taeda ............... | H01M 10/0569 |
| 2017/0110723 | A1 | 4/2017 | Ishibashi et al. | |
| 2017/0214087 | A1* | 7/2017 | Yoshida ................ | H01M 4/525 |
| 2018/0358610 | A1* | 12/2018 | Shimanuki ............ | H01M 4/622 |

FOREIGN PATENT DOCUMENTS

| | | | | |
|---|---|---|---|---|
| CN | 106133989 | A | 11/2016 | |
| EP | 2216844 | A2 | 8/2010 | |
| EP | 2894698 | A1 | 7/2015 | |
| JP | 2003-086244 | A | 3/2003 | |
| JP | 2004-296115 | A | 10/2004 | |
| JP | 2007-027100 | A | 2/2007 | |
| JP | 2009-135076 | A | 6/2009 | |
| JP | 2009-170146 | A | 7/2009 | |
| JP | 2009-277597 | A | 11/2009 | |
| JP | 2009-302051 | A | 12/2009 | |
| JP | 2010-102868 | A | 5/2010 | |
| JP | 2010-153331 | A | 7/2010 | |
| JP | 2010-529634 | A | 8/2010 | |
| JP | 2010-192127 | A | 9/2010 | |
| JP | 2012-059486 | A | 3/2012 | |
| JP | 2012-155985 | A | 8/2012 | |
| JP | 2013-016456 | A | 1/2013 | |
| JP | 2013-080726 | A | 5/2013 | |
| JP | 2013-168361 | A | 8/2013 | |
| JP | 2015-046221 | A | 3/2015 | |
| WO | 2005/011043 | A1 | 2/2005 | |
| WO | 2008/132792 | A1 | 11/2008 | |
| WO | 2014/054355 | A1 | 4/2014 | |
| WO | 2015/053177 | A1 | 4/2015 | |
| WO | WO-2015146684 | A1 * | 10/2015 | ............. H01G 11/64 |
| WO | WO-2015146685 | A1 * | 10/2015 | ........ H01M 10/0525 |
| WO | WO-2015199063 | A1 * | 12/2015 | ............ H01M 4/587 |
| WO | WO-2017094712 | A1 * | 6/2017 | ........ H01M 10/0567 |
| WO | 2017/204213 | A1 | 11/2017 | |

OTHER PUBLICATIONS

International Search Report for PCT/JP2018/016566, dated Jul. 10, 2018.
Chinese Office Action for CN Application No. 201880026844.X dated Nov. 9, 2021 with English Translation.
Chinese Office Action for CN Application No. 201880026844.X dated May 25, 2022 with English Translation.
CN Office Communication for CN Application No. 201880026844.X, dated Aug. 26, 2022 with English Translation.

* cited by examiner

LITHIUM ION SECONDARY BATTERY INCLUDING POROUS INSULATING LAYER FORMED ON POSITIVE ELECTRODE AND ELECTROLYTE SOLUTION HAVING HALOGENATED CYCLIC ACID ANHYDRIDE

CROSS REFERENCE TO RELATED APPLICATIONS

This application is a National Stage of International Application No. PCT/JP2018/016566 filed Apr. 24, 2018, claiming priority based on Japanese Patent Application No. 2017-086233 filed Apr. 25, 2017, the entire disclosure of which is hereby incorporated by reference.

TECHNICAL FIELD

The present invention relates to a lithium ion secondary battery, a manufacturing method for a lithium ion secondary battery and a vehicle equipped with a lithium ion secondary battery.

BACKGROUND ART

Lithium ion secondary batteries are used in various applications. Accordingly, there is a demand for a lithium ion secondary battery that has high energy density and good life characteristics. One method for improving the life characteristics is to add an additive to the electrolyte solution to form a SEI film on the electrode. This is considered to be because the SEI film suppresses decomposition of the electrolyte solution on an electrode surface. In order to further improve life characteristics, halogenated cyclic acid anhydrides have been studied as additives. Patent Document 1 discloses that the capacity retention rate of a battery can be improved by using a fluorinated cyclic acid anhydride as an additive.

CITATION LIST

Patent Literature

Patent document 1: Japanese patent laid-open 2004-296115

SUMMARY OF INVENTION

Technical Problem

The halogenated cyclic acid anhydride has a high improving effect on capacity retention rate. However, the lithium ion secondary battery using the halogenated cyclic acid anhydride has a problem that internal resistance is greatly increased after charge/discharge cycles. In view of the above problem, a purpose of the present invention is to provide a lithium ion secondary battery comprising the halogenated cyclic anhydride as an electrolyte additive, in which the increase in internal resistance is suppressed.

Solution to Problem

The first lithium ion secondary battery according to the present invention is characterized in that it comprises a positive electrode and an electrolyte solution, wherein a porous layer comprising an insulating filler is formed on the positive electrode, and the electrolyte solution comprises 0.005 to 10 weight % of a halogenated cyclic acid anhydride.

Advantageous Effects of Invention

According to one embodiment of the present invention, it is possible to provide a lithium ion secondary battery with a small increase in internal resistance.

DESCRIPTION OF EMBODIMENTS

Figure 1:
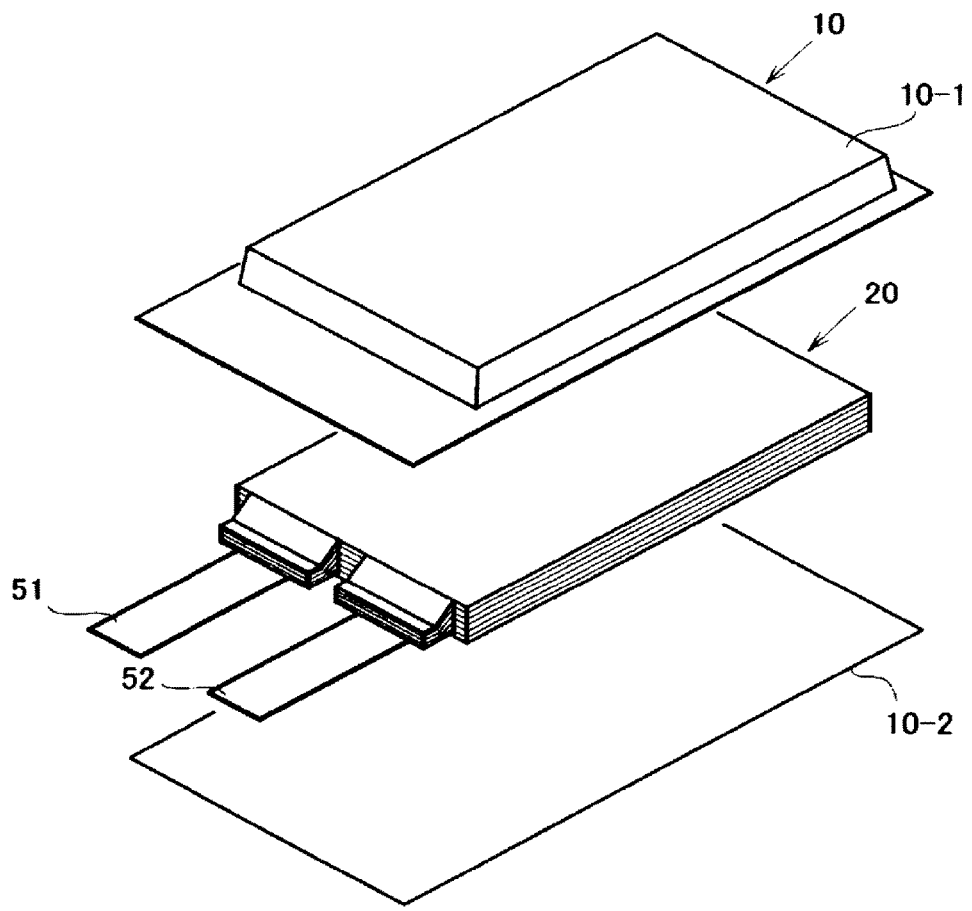
FIG. 1 is an exploded perspective view showing a basic structure of a film package battery.

Hereinafter, one example of the lithium ion secondary battery of the present embodiment will be described for each component.

<Positive Electrode>

The positive electrode comprises a positive electrode current collector, a positive electrode active material layer comprising a positive electrode active material and a positive electrode binder, and a porous layer comprising an insulating filler.

The positive electrode active material may be selected from some viewpoints. From the viewpoint of high energy density, it is preferable to contain a compound having high capacity. Examples of the high capacity compound include lithium nickelate ($LiNiO_2$) and lithium nickel composite oxides in which a part of the Ni of lithium nickelate is replaced by another metal element, and layered lithium nickel composite oxides represented by the following formula (C) are preferred.

$$Li_yNi_{(1-x)}M_xO_2 \qquad (C)$$

wherein 0 x≤1, 0<y≤1.2, and M is at least one element selected from the group consisting of Co, Al, Mn, Fe, Ti, and B.

From the viewpoint of high capacity, it is preferred that the content of Ni is high, that is, x is less than 0.5, further preferably 0.4 or less in the formula (C). Examples of such compounds include $Li_\alpha Ni_\beta Co_\gamma Mn_\delta O_2$ (0<α≤1.2, preferably 1≤α≤1.2, β+γ+δ=1, β≥0.7, and γ≤0.2) and $Li_\alpha Ni_\beta Co_\gamma Al_\delta O_2$ (0<α≤1.2, preferably 1≤α≤1.2, β+γ+δ=1, β≥0.6, preferably β≥0.7, and γ≤0.2) and particularly include $LiNi_\beta Co_\gamma Mn_\delta O_2$ (0.75≤β≤0.85, 0.05≤γ≤0.15, and 0.10≤δ≤0.20). More specifically, for example, $LiNi_{0.8}Co_{0.05}Mn_{0.15}O_2$, $LiNi_{0.8}Co_{0.1}Mn_{0.1}O_2$, $LiNi_{0.8}Co_{0.15}Al_{0.05}O_2$, and $LiNi_{0.8}Co_{0.1}Al_{0.1}O_2$ may be preferably used.

From the viewpoint of thermal stability, it is also preferred that the content of Ni does not exceed 0.5, that is, x is 0.5 or more in the formula (C). In addition, it is also preferred that particular transition metals do not exceed half. Examples of such compounds include $Li_\alpha Ni_\beta Co_\gamma Mn_\delta O_2$ (0<α≤1.2, preferably 1≤α≤1.2, β+γ+δ=1, 0.2≤β≤0.5, 0.1≤γ≤0.4, and 0.1≤δ≤0.4). More specific examples may include $LiNi_{0.4}Co_{0.3}Mn_{0.3}O_2$ (abbreviated as NCM433), $LiNi_{1/3}Co_{1/3}Mn_{1/3}O_2$, $LiNi_{0.5}Co_{0.2}Mn_{0.3}O_2$ (abbreviated as NCM523), and $LiNi_{0.5}Co_{0.3}Mn_{0.2}O_2$ (abbreviated as NCM532) (also including those in which the content of each transition metal fluctuates by about 10% in these compounds).

In addition, two or more compounds represented by the formula (C) may be mixed and used, and, for example, it is also preferred that NCM532 or NCM523 and NCM433 are mixed in the range of 9:1 to 1:9 (as a typical example, 2:1) and used. Further, by mixing a material in which the content of Ni is high (x is 0.4 or less in the formula (C)) and a material in which the content of Ni does not exceed 0.5 (x is 0.5 or more, for example, NCM433), a battery having high capacity and high thermal stability can also be formed.

The layered lithium nickel composite oxide may be further replaced by another metal element. For example, a layered lithium nickel composite oxide represented by the following formula (D) may be preferably used.

$$Li_aNi_bCo_cM1_dM2_eO_f \qquad (D)$$

wherein $0.8 \leq a \leq 1.2$, $0.5 \leq b < 1.0$, $0.005 \leq c \leq 0.4$, $0.005 \leq d \leq 0.4$, $0 \leq e < 0.1$, $1.8 \leq f \leq 2.3$, $b+c+d+e=1$, M1 is Mn or Al, and M2 is one or more metals selected from the group consisting of B, Na, Mg, Al, S, K, Ca, Ti, V, Cr, Fe, Cu, Zn, Zr, Nb, Mo, Sn, Pb and W.

Examples of the positive electrode active materials other than the above include lithium manganate having a layered structure or a spinel structure such as $LiMnO_2$, $Li_xMn_2O_4$ ($0<x<2$), $Li_2MnO_3$, $xLi_2MnO_3-(1-x)LiMO_2$ ($0.1<x<0.8$, and M is one or more elements selected from the group consisting of Mn, Fe, Co, Ni, Ti, Al and Mg) and $Li_xMn_{1.5}Ni_{0.5}O_4$ ($0<x<2$); $LiCoO_2$ or materials in which a part of the transition metal in this material is replaced by other metal(s); materials in which Li is excessive as compared with the stoichiometric composition in these lithium transition metal oxides; materials having an olivine structure such as $LiFePO_4$; and the like. In addition, materials in which a part of elements in these metal oxides is substituted by Al, Fe, P, Ti, Si, Pb, Sn, In, Bi, Ag, Ba, Ca, Hg, Pd, Pt, Te, Zn, La or the like are also usable. The positive electrode active materials described above may be used alone or in combination of two or more.

The positive electrode binder is not particularly limited, and polyvinylidene fluoride, vinylidene fluoride-hexafluoropropylene copolymer, vinylidene fluoride-tetrafluoroethylene copolymer, polytetrafluoroethylene, polypropylene, polyethylene, polybutadiene, polyacrylic acid, polyacrylic ester, polystyrene, polyacrylonitrile, polyimide, polyamide-imide and the like may be used. Also, the positive electrode binder may be a mixture, a copolymer or a cross-linked body of a plurality of the above resins, for example, styrene butadiene rubber (SBR). When an aqueous binder such as an SBR emulsion is used, a thickener such as carboxymethyl cellulose (CMC) can also be used. The lower limit of the amount of the positive electrode binder is preferably 1 part by weight or more, and more preferably 2 parts by weight or more, and the upper limit is preferably 30 parts by weight or less, and more preferably 25 parts by weight or less, based on 100 parts by weight of the positive electrode active material.

For the positive electrode active material layer, a conductive assisting agent may be added for the purpose of lowering the impedance. Examples of the conductive assisting agent include, flake-like, soot, and fibrous carbon fine particles and the like, for example, graphite, carbon black, acetylene black, vapor grown carbon fibers and the like.

As the positive electrode current collector, from the view point of electrochemical stability, aluminum, nickel, copper, silver, and alloys thereof are preferred. As the shape thereof, foil, flat plate, mesh and the like are exemplified. In particular, a positive electrode current collector using aluminum, an aluminum alloy, or iron-nickel-chromium-molybdenum based stainless steel is preferable.

The positive electrode may be prepared, for example, by preparing a positive electrode slurry comprising the positive electrode active material, the positive electrode binder and a solvent, and applying this to the positive electrode current collector to form the positive electrode active material layer. Examples of a method of forming the positive electrode active material layer include a doctor blade method, a die coater method, a CVD method, a sputtering method, and the like. After forming the positive electrode active material layer in advance, a thin film of aluminum, nickel or an alloy thereof as a positive electrode current collector may be formed thereon by a method such as vapor deposition or sputtering, to prepare a positive electrode.

In the present embodiment, the porous layer (hereinafter, it is also referred to as an insulating layer) comprising an insulating filler is provided on the positive electrode. The insulating layer is preferably laminated on the positive electrode active material layer. The insulating layer, which is provided on the positive electrode, can reduce the decomposition of the electrolyte solution caused by the positive electrode active material. In addition, when the battery comprises the halogenated cyclic acid anhydride, an increase in resistance can be largely reduced by providing the insulating layer on the positive electrode.

Examples of the insulating filler include metal oxides and nitrides, specifically inorganic particles, for example, aluminum oxide (alumina), silicon oxide (silica), titanium oxide (titania), zirconium oxide (zirconia), magnesium oxide (magnesia), zinc oxide, strontium titanate, barium titanate, aluminum nitride, silicon nitride and the like, and organic particles, for example, polypropylene, polyethylene, polyesters such as polyethylene terephthalate, aramid, polyimide, polyamide-imide, silicone rubber and the like.

In addition to the insulating filler, the insulating layer may comprise a binder for binding the insulating filler. Examples of the binder include, but not particular limited to, polymers containing a halogen such as fluorine or chlorine. These are excellent in oxidation resistance, and therefore suitable for the binder used in the insulating layer. More specifically, such binders include polyolefins containing fluorine or chlorine, such as polyvinylidene fluoride (PVdF), polytetrafluoroethylene (PTFE), polyhexafluoropropylene (PHFP), polytrifluorinated chlorinated ethylene (PCTFE), polyperfluoroalkoxyfluoroethylene.

When a water-based solvent (a solution using water or a mixed solvent mainly containing water as a dispersion medium of a binder) is used in a coating material for forming the insulating layer, which will be described later, a polymer dispersible or soluble in the water-based solvent may be used as the binder. As the polymer dispersible or soluble in the water-based solvent, for example, an acrylic resin can be exemplified. As the acrylic resins, homopolymers obtained by polymerizing one monomer, such as acrylic acid, methacrylic acid, acrylamide, methacrylamide, 2-hydroxyethyl acrylate, 2-hydroxyethyl methacrylate, methyl methacrylate, ethylhexyl acrylate, or butyl acrylate, are preferably used. Also, the acrylic resin may be a copolymer obtained by polymerizing two or more of the above monomers. Furthermore, it may be a mixture of two or more of the above homopolymers and the copolymers. In addition to the above-mentioned acrylic resins, polyolefin resins, such as styrene butadiene rubber (SBR) and polyethylene (PE), polytetrafluoroethylene (PTFE), and the like can be used. These polymers can be used singly or in combination of two or more. The form of the binder is not particularly limited, and those in the form of particles (powder) may be used as they are, or those prepared in a solution state or an emulsion state may be used. Two or more kinds of the binders may be used in different forms respectively.

Besides these, those exemplified as binders used in an electrode may be used as a binder for the insulating layer.

The insulating layer may contain materials other than the above mentioned insulating filler and binder, if necessary. Examples of such a material include various polymer materials that can function as thickeners for the coating materials for forming the insulating layer, for example, carboxymethyl cellulose (CMC), methyl cellulose (MC) and the like. In particular, when the water-based solvent is used, it is preferable to contain the polymer that can function as a thickener.

The ratio of the insulating filler in the insulating layer is preferably 80 weight % or more, and more preferably 90 weight % or more. The ratio of the insulating filler in the insulating layer is preferably 99 weight % or less, and more preferably 97 weight % or less. Also, the ratio of the binder in the insulating layer is preferably 0.1 weight % or more, and more preferably 1 weight % or more. The ratio of the binder in the insulating layer is preferably 20 weight % or less, and more preferably 10 weight % or less. If the ratio of the binder is too low, the strength (shape retentively) of the insulating layer itself is lowered, and problems such as cracking and peeling may occur. If the ratio of the binder is too high, gaps between the particles in the insulating layer may become insufficient, and the ion permeability of the insulating layer may decrease in some cases. Appropriate porosity can be obtained by setting the ratios of the insulating filler and the binder within the above ranges.

In the case where a component for forming the insulating layer, for example a thickener, other than the inorganic filler and the binder is contained, the content ratio of the thickener in the insulating layer is preferably about 10 weight % or less, preferably about 5 weight % or less, and preferably about 2 weight % or less (for example, approximately 0.5 weight % to 1 weight %).

To maintain ion conductivity, the porosity (voidage) (the ratio of the porosity volume to the apparent volume) of the insulating layer is preferably 20% or more, and more preferably 30% or more. However, when the porosity is too high, falling off or cracking occurs due to friction or shock to the insulating layer. Therefore, the porosity of the insulating layer is preferably 80% or less, and more preferably 70% or less.

The porosity can be determined by calculating the theoretical density and the apparent density from the weight per unit area of the insulating layer, the ratios and the true specific gravity of the materials constituting the insulating layer, and the coating thickness.

Next, a method of forming the insulating layer will be described. The insulating layer can be formed, for example, by applying the coating materials for forming the insulating layer to the positive electrode, but the method of forming the insulating layer is not particularly limited to this. As the coating material for forming the insulating layer, paste-like material (including slurry or ink state material) in which components of the insulating layer, such as the insulating filler and the binder, and a solvent are mixed and dispersed may be used.

As solvents used in the coating material for forming the insulating layer, water and a mixed solvent mainly containing water are exemplified. As solvents other than water constituting such a mixed solvent, one or two or more kinds of organic solvents (lower alcohol, lower ketone, etc.) that can be uniformly mixed with water can be selected appropriately and used. Alternatively, it may be an organic solvent such as N-methylpyrrolidone (NMP), pyrrolidone, methyl ethyl ketone, methyl isobutyl ketone, cyclohexanone, toluene, dimethylformamide, dimethylacetamide, or a combination of two or more thereof. The content of the solvent in the coating material for forming the insulating layer is not particularly limited, but it is preferably 30 to 90 weight %, particularly 50 to 70 weight % of the coating material as whole.

The operation of mixing components, such as the insulating filler and binder, into the solvent can be carried out by using a suitable kneader such as a ball mill, a homodisper, Dispermill (registered trademark), Clearmix (registered trademark), Filmix (registered trademark), or a ultrasonic disperser.

The insulating layer can be prepared by applying the coating material for forming the insulating layer to the positive electrode active material layer. The coating material for forming the insulating layer may be applied at the same time as the positive electrode slurry is applied to the positive electrode current collector. The operation of applying the coating material for forming the insulating layer can be carried out by a conventional general coating means. For example, a suitable amount of the coating material for forming the insulating layer can be applied to form a coating having a uniform thickness using a suitable coating apparatus (e.g., gravure coater, slit coater, die coater, comma coater, dip coater). Thereafter, the coating is dried by a suitable drying means, and the solvent may be removed. The drying temperature may be 140° C. or lower, for example, 30 to 110° C. When the insulating layer does not comprise the binder, a step of sintering or fusion-bonding the insulating filler may be further provided so that the insulating filler will be fixed.

<Negative Electrode>

The negative electrode comprises a negative electrode current collector and a negative electrode active material layer comprising a negative electrode active material and a negative electrode binder.

The negative electrode active material is not particularly limited as long as it is a material capable of reversibly intercalating and deintercalating lithium ions upon charge/discharge. Specifically, metals, metal oxides, carbon materials and the like may be exemplified.

Examples of the metal include Li, Al, Si, Pb, Sn, In, Bi, Ag, Ba, Ca, Hg, Pd, Pt, Te, Zn, La, alloys of two or more of these and the like. In addition, two or more of these metals and alloys may be mixed and used. These metals and alloys may comprise one or more non-metal elements.

Examples of the metal oxide include silicon oxide, aluminum oxide, tin oxide, indium oxide, zinc oxide, lithium oxide, and composites of these. In the present embodiment, tin oxide or silicon oxide is preferably contained as a metal oxide negative electrode active material, and silicon oxide is more preferably contained. This is because silicon oxide is relatively stable and is unlikely to trigger a reaction with other compounds. As silicon oxide, those represented by the composition formula $SiO_x$ ($0<x\leq2$) are preferred. Also, for example, 0.1 to 5 weight % of one or two or more elements selected from nitrogen, boron, and sulfur can be added to the metal oxide. In this way, the electroconductivity of the metal oxide can be enhanced.

The surface of the metal and metal oxide may be coated with carbon. The carbon coating may improve cycle characteristics. Examples of a method for forming the carbon coating include a sputtering method, a vapor deposition method and the like using a carbon source.

Examples of the carbon material include graphite, amorphous carbon, graphene, diamond-like carbon, carbon nanotube, and composites thereof. Here, highly crystalline graphite is highly electroconductive, and has excellent adhesion to a negative electrode current collector composed of a metal such as copper as well as voltage flatness. On the other hand, low-crystallinity amorphous carbon shows relatively small volume expansion, is thus highly effective in lessening the volume expansion of the entire negative electrode, and is unlikely to undergo degradation resulting from non-uniformity such as grain boundaries and defects.

The negative electrode binder is not particularly limited, and polyvinylidene fluoride (PVdF), vinylidene fluoride-hexafluoropropylene copolymer, vinylidene fluoride-tetrafluoroethylene copolymer, polytetrafluoroethylene, polypropylene, polyethylene, polybutadiene, polyacrylic acid, polyacrylic ester, polystyrene, polyacrylonitrile, polyimide, polyamide-imide or the like may be used. Also, the negative electrode binder includes mixtures, copolymers or cross-linked bodies of a plurality of the above resins, for example, styrene butadiene rubber (SBR). When an aqueous binder such as an SBR emulsion is used, a thickener such as carboxymethyl cellulose (CMC) can also be used. The amount of the negative electrode binder is preferably 0.5 to 20 parts by weight based on 100 parts by weight of the negative electrode active material, from the viewpoint of the sufficient binding strength and the high energy density being in a trade-off relation with each other.

For the negative electrode active material layer, a conductive assisting agent may be added for the purpose of lowering the impedance. Examples of the conductive assisting agent include, flake-like, soot, and fibrous carbon fine particles and the like, for example, graphite, carbon black, acetylene black, vapor grown carbon fibers and the like.

As the negative electrode current collector, from the viewpoint of electrochemical stability, aluminum, nickel, stainless steel, chrome, copper, silver, or an alloy thereof may be used. As the shape thereof, foil, flat plate, mesh and the like are exemplified.

The negative electrode according to the present embodiment may be prepared, for example, by preparing a negative electrode slurry comprising the negative electrode active material, the negative electrode binder and a solvent, and applying this to the negative electrode current collector to form the negative electrode active material layer. Examples of a method for forming the negative electrode active material layer include a doctor blade method, a die coater method, a CVD method, a sputtering method, and the like. After forming the negative electrode active material layer in advance, a thin film of aluminum, nickel or an alloy thereof as a positive electrode current collector may be formed thereon by a method such as vapor deposition or sputtering, to prepare a negative electrode. Similarly to the positive electrode, an insulating layer may be provided on the negative electrode.

<Electrolyte Solution>

The electrolyte solution comprises the halogenated cyclic acid anhydride as an additive in addition to a non-aqueous solvent and a supporting salt.

In the present embodiment, examples of the halogenated cyclic acid anhydride include, but not particularly limited to, carboxylic acid anhydrides, sulfonic acid anhydrides, and carboxylic sulfonic anhydrides.

It is presumed that the acid anhydride in which at least one hydrogen atom has been replaced with halogen has high oxidation resistance and can reduce the oxidative decomposition at the positive electrode. The halogen substitution ratio of the halogenated cyclic acid anhydride {i.e., (the number of halogen atoms)/(the total number of hydrogen atoms and halogen atoms)} is preferably high. The halogen substitution ratio of the halogenated cyclic acid anhydride is preferably 25% or more, more preferably 50% or more and most preferably 100%.

The halogen is preferably fluorine. It is presumed that the acid anhydride in which at least one hydrogen atom has been replaced with a fluorine atom has high oxidation resistance and can reduce the oxidative decomposition at the positive electrode. The fluorine substitution ratio of the fluorinated acid anhydride {i.e., (the number of fluorine atoms)/(the total number of hydrogen atoms and fluorine atoms)} is preferably high. The fluorine substitution ratio of the fluorinated acid anhydride is preferably 25% or more, more preferably 50% or more and most preferably 100%.

In the present embodiment, the halogenated cyclic acid anhydride is preferably a carboxylic acid anhydride represented by the following formula (1).

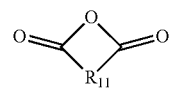

(1)

In formula (1), $R_{11}$ is a substituted or unsubstituted alkylene group having 1 to 5 carbon atoms, a substituted or unsubstituted alkenylene group having 2 to 5 carbon atoms, a substituted or unsubstituted cycloalkan-diyl group having 5 to 12 carbon atoms, a substituted or unsubstituted cycloalken-diyl group having 5 to 12 carbon atoms, a substituted or unsubstituted benzene-diyl group, or a divalent group having 2 to 6 carbon atoms in which alkylene groups are bonded via an ether bond, with the proviso that at least part of the hydrogen atoms in $R_{11}$ are replaced by halogen.

In the formula (1), the alkylene group and the alkenylene group for $R^{11}$ may be straight chain or branched.

In the formula (1), the number of carbon atoms in the alkylene group for $R_{11}$ is preferably 1, 2, 3 or 4. The number of carbon atoms in the alkenylene group for $R_{11}$ is preferably 2, 3 or 4.

In the formula (1), the number of carbon atoms in the cycloalkan-diyl group and the cycloalken-diyl group for $R_{11}$ is preferably 5, 6, 7, 8, 9 or 10. Herein, the cycloalkan-diyl group and the cycloalken-diyl group may be a divalent group having a plurality of ring structures such as bicycloalkylene group or bicycloalkenylene group.

In the formula (1), the divalent group having 2 to 6 carbon atoms in which alkylene groups are bonded via an ether bond represents a divalent group in which two or more alkylene groups are bonded via ether bond(s) (—O—), wherein two or more alkylene groups may be either the same or different. The alkylene group may have a branched chain. The total number of carbon atoms of two or more alkylene groups is preferably 2, 3, 4 or 5, and more preferably 2, 3 or 4.

In the formula (1), $R_{11}$ is more preferably a substituted or unsubstituted alkylene group having 2 to 5 carbon atoms, or a substituted or unsubstituted alkenylene group having 2 to 5 carbon atoms. $R_{11}$ is still more preferably a substituted or unsubstituted alkylene group having 2 to 3 carbon atoms, or a substituted or unsubstituted alkenylene group having 2 to 3 carbon atoms.

Further, in the formula (1), it is more preferable that the carbon skeleton (carbon-carbon bonds) in $R_{11}$ is constituted all by single bonds. This is seemingly because that gas generation caused by an excessive reaction is reduced as compared with the case containing a double bond in $R_{11}$. For example, $R_{11}$ is more preferably an alkylene group.

In the formula (1), substituents for $R_{11}$ include, for example, alkyl groups having 1 to 5 carbon atoms (for example, methyl group, ethyl group, propyl group, isopropyl group, butyl group), alkenyl groups having 2 to 6 carbon atoms (for example, vinyl group, 1-propenyl group, 2-propenyl group, 2-butenyl group), aryl groups (for example, phenyl group, benzyl group, tolyl group and xylyl group), alkoxy groups having 1 to 5 carbon atoms (for example, methoxy group, ethoxy group, n-propoxy group, isopropoxy group, n-butoxy group, tert-butoxy group), amino groups (including dimethylamino group, methylamino group), carboxy group, hydroxy group, vinyl group, cyano group and the like. R ii may have one substituent or may have a plurality of substituents.

Specific examples of the halogenated cyclic acid anhydride represented by formula (1) include, but not limited to, halides of succinic anhydride, glutaric anhydride, maleic anhydride, citraconic anhydride, glutaconic anhydride, itaconic anhydride, diglycolic anhydride, phenyl succinic anhydride, 2-phenyl glutaric anhydride, 1,2-cyclohexanedicarboxylic anhydride, 1,2,3,4-cyclopentane tetracarboxylic dianhydride, 4-cyclohexene-1,2-dicarboxylic anhydride, 3,4,5,6-tetrahydrophthalic anhydride, 5-norbornene-2,3-dicarboxylic anhydride, phthalic anhydride, and pyromellitic anhydride and the like. These may be used alone or in combination of two or more.

In formula (1), the halogen to substitute hydrogens is preferably fluorine. Specific examples of the fluorinated cyclic carboxylic acid anhydride include fluorides of the above cyclic acid anhydrides. In particular, a compound obtained by substituting all hydrogens of an unsubstituted cyclic carboxylic acid anhydride with fluorine is preferred.

Among the halogenated cyclic acid anhydrides represented by formula (1), a fluorinated glutaric anhydride is preferred, and hexafluoroglutaric anhydride is particularly preferred. The effect of suppressing the increase in resistance is particularly high in a battery using the fluorinated glutaric anhydride. In addition, a battery having a high capacity retention rate can be obtained by using the fluorinated glutaric anhydride.

The concentration of the halogenated cyclic acid anhydride in the electrolyte solution is 0.005 to 10 weight %. When the concentration of the halogenated cyclic acid anhydride is 0.005 weight % or more, a film derived from the halogenated cyclic acid anhydride can be formed effectively. In addition, moisture in the negative electrode can be captured effectively. When the concentration of the halogenated cyclic acid anhydride is 10 weight % or less, the film caused by decomposition of the halogenated cyclic acid anhydride can be prevented from being formed to large thickness, and an increase in resistance caused by the film can be suppressed. The concentration of the halogenated cyclic acid anhydride in the electrolyte solution is preferably 0.01 weight % or more, and more preferably 0.05 weight % or more. Also, the concentration of the halogenated cyclic acid anhydride in the electrolyte solution is preferably 8 weight % or less, and more preferably 5 weight % or less.

Examples of the non-aqueous solvent include aprotic organic solvents, for examples, cyclic carbonates such as propylene carbonate (PC), ethylene carbonate (EC) and butylene carbonate (BC); open-chain carbonates such as dimethyl carbonate (DMC), diethyl carbonate (DEC), ethyl methyl carbonate (EMC) and dipropyl carbonate (DPC); carbonate derivatives; aliphatic carboxylic acid esters such as methyl formate, methyl acetate and ethyl propionate; ethers such as diethyl ether and ethyl propyl ether; phosphoric acid esters such as trimethyl phosphate, triethyl phosphate, tripropyl phosphate, trioctyl phosphate and triphenyl phosphate; fluorinated aprotic organic solvents obtainable by substituting at least part of hydrogen atoms of these compounds with fluorine atom(s); and the like.

Among them, a cyclic or open-chain carbonate(s) such as ethylene carbonate (EC), propylene carbonate (PC), butylene carbonate (BC), dimethyl carbonate (DMC), diethyl carbonate (DEC), ethyl methyl carbonate (EMC), dipropyl carbonate (DPC) or the like is preferably contained.

The non-aqueous solvent may be used alone, or in combination of two or more.

The supporting salt is not particularly limited except that it comprises Li. Examples of the supporting salt include $LiPF_6$, $LiAsF_6$, $LiAlCl_4$, $LiClO_4$, $LiBF_4$, $LiSbF_6$, $LiCF_3SO_3$, $LiC_4F_9SO_3$, $LiC(CF_3SO_2)_3$, $LiN(FSO_2)_2$ (abbreviated as LiFSI), $LiN(CF_3SO_2)_2$, $LiN(C_2F_5SO_2)_2$, $LiB_{10}Cl_{10}$ and the like. Besides these, the supporting salt includes lower aliphatic lithium carboxylate, chloroboran lithium, lithium tetraphenylborate, LiBr, LiI, LiSCN, LiCl and the like. Among these, $LiPF_6$ and LiFSI are particularly preferred from the viewpoint of oxidation resistance, reduction resistance, stability and solubility. The supporting salts may be used alone or in combination of two or more. The amount of the supporting salt is preferably 0.4 mol or more and 1.5 mol or less, more preferably 0.5 mol or more and 1.2 mol or less with respect to 1 L of the electrolyte solvent.

<Separator>

Since the positive electrode having the insulating layer is used, the lithium ion secondary battery according to the present embodiment may not necessarily comprise a separator. A separator may be used together with the positive electrode having the insulating layer.

The separator may be of any type as long as it has durability against the electrolyte solution. Specific examples of a material thereof include polyolefins such as polypropylene and polyethylene, cellulose, polyesters such as polyethylene terephthalate and polybutylene terephthalate, polyimide, polyamide-imide, polyvinylidene fluoride, aromatic polyamides (aramid) such as polymetaphenylene isophthalamide, polyp araphenylene terephthalamide and copolyparaphenylene 3,4'-oxydiphenylene terephthalamide, and the like. These can be used as porous films, woven fabrics, nonwoven fabrics or the like.

<Structure of Secondary Battery>

Figure 2:
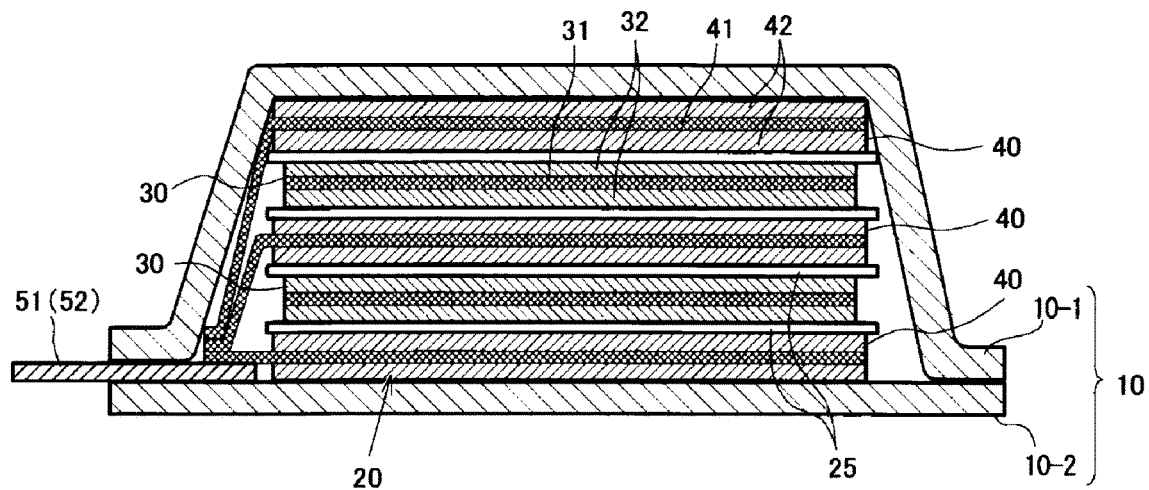
FIG. 2 is a cross-sectional view schematically showing a cross section of the battery of FIG. 1.

The lithium ion secondary battery according to the present embodiment may have, for example, a structure as shown in FIGS. 1 and 2. This secondary battery comprises a battery element 20, a film outer package 10 housing the battery element 20 together with an electrolyte, and a positive electrode tab 51 and a negative electrode tab 52 (hereinafter these are also simply referred to as "electrode tabs").

Figure 3:
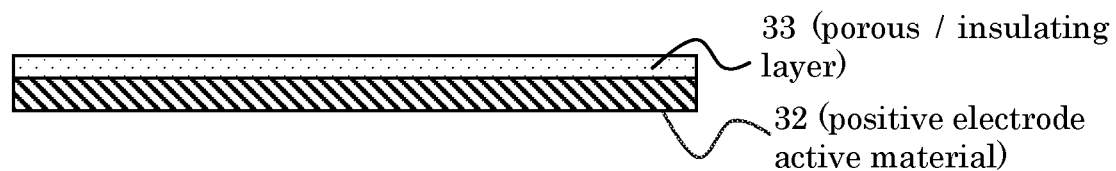
FIG. 3 is a cross-sectional view showing a cross section of a portion of the battery in FIG. 1.

In the battery element 20, a plurality of positive electrodes 30 and a plurality of negative electrodes 40 are alternately stacked with separators 25 sandwiched therebetween as shown in FIG. 2. In the positive electrode 30, an electrode material 32 is applied to both surfaces of a metal foil 31, and also in the negative electrode 40, an electrode material 42 is applied to both surfaces of a metal foil 41 in the same manner. As shown in FIG. 3, an insulating layer 33 can be formed on the layer 32 of the electrode active material. The present invention is not necessarily limited to stacking type batteries and may also be applied to batteries such as a winding type.

As shown in FIGS. 1 and 2, the lithium ion secondary battery according to the present embodiment may have an arrangement in which the electrode tabs are drawn out to one side of the outer package, but the electrode tab may be drawn out to both sides of the outer package. Although detailed illustration is omitted, the metal foils of the positive electrodes and the negative electrodes each have an extended portion in part of the outer periphery. The extended portions of the negative electrode metal foils are brought together into one and connected to the negative electrode tab 52, and the extended portions of the positive electrode metal foils are brought together into one and connected to the positive electrode tab 51 (see FIG. 2). The portion in which the extended portions are brought together into one in the stacking direction in this manner is also referred to as a "current collecting portion" or the like.

The film outer package 10 is composed of two films 10-1 and 10-2 in this example. The films 10-1 and 10-2 are heat-sealed to each other in the peripheral portion of the battery element 20 and hermetically sealed. In FIG. 1, the positive electrode tab 51 and the negative electrode tab 52 are drawn out in the same direction from one short side of the film outer package 10 hermetically sealed in this manner.

Of course, the electrode tabs may be drawn out from different two sides respectively. In addition, regarding the arrangement of the films, in FIG. 1 and FIG. 2, an example in which a cup portion is formed in one film 10-1 and a cup portion is not formed in the other film 10-2 is shown, but other than this, an arrangement in which cup portions are formed in both films (not illustrated), an arrangement in which a cup portion is not formed in either film (not illustrated), and the like may also be adopted.

<Method for Manufacturing Secondary Battery>

The lithium ion secondary battery according to the present embodiment can be manufactured by a conventional method. An example of a method for manufacturing a lithium ion secondary battery will be described taking a stacked laminate type lithium ion secondary battery as an example. First, in the dry air or an inert atmosphere, the positive electrode and the negative electrode are placed to oppose to each other via a separator to form an electrode element. Next, this electrode element is accommodated in an outer package (container), an electrolyte solution is injected, and the electrodes are impregnated with the electrolyte solution. Thereafter, the opening of the outer package is sealed to complete the lithium ion secondary battery.

<Assembled Battery>

A plurality of the lithium ion secondary batteries according to the present embodiment may be combined to form an assembled battery. The assembled battery may be configured by connecting two or more lithium ion secondary batteries according to the present embodiment in series or in parallel or in combination of both. The connection in series and/or parallel makes it possible to adjust the capacitance and voltage freely. The number of the lithium ion secondary batteries included in the assembled battery can be set appropriately according to the battery capacity and output.

<Vehicle>

The lithium ion secondary battery or the assembled battery according to the present embodiment can be used in vehicles. Vehicles according to the present embodiment include hybrid vehicles, fuel cell vehicles, electric vehicles (besides four-wheel vehicles (cars, commercial vehicles such as trucks and buses, light automobiles, etc.), two-wheeled vehicle (bike) and tricycle), and the like. The vehicles according to the present embodiment are not limited to automobiles, and it may be a variety of power source of other vehicles, such as a moving body like a train, a ship, a submarine, a satellite.

EXAMPLES

Example 1

Production of the battery of this example and evaluation of the produced battery will be described.

(Positive Electrode)

Lithium nickel composite oxide ($LiNi_{0.80}Mn_{0.15}Co_{0.05}O_2$) as a positive electrode active material, carbon black as a conductive assisting agent, and polyvinylidene fluoride as a positive electrode binder were weighed at a weight ratio of 90:5:5, and were kneaded with N-methylpyrrolidone to prepare a positive electrode slurry. The prepared positive electrode slurry was applied to a 20 μm-thick aluminum foil as a positive electrode current collector, dried and further pressed to produce a positive electrode.

(Preparation of Coating Material for Forming Insulating Layer)

Next, alumina (average particle diameter: 1.0 μm) and polyvinylidene fluoride (PVdF) were weighed at a weight ratio of 90:10, and were kneaded with N-methylpyrrolidone to prepare a coating material for forming an insulating layer.

(Insulating Layer Coating on Positive Electrode)

The prepared coating material for forming an insulating layer was applied onto the positive electrode with a die coater, dried, and further pressed to obtain a positive electrode coated with an insulating layer. When the cross section was observed by an electron microscope, the average thickness of the insulating layer was 5 μm. The porosity of the insulating layer was calculated as 55% from the average thickness of the insulating layer, and the true density and the composition ratio of each material constituting the insulating layer.

(Negative Electrode)

Artificial graphite particles (average particle diameter 8 μm) as a negative electrode active material, carbon black as a conductive assisting agent, and a 1:1 mixture, by weight, of styrene butadiene copolymer rubber and carboxymethyl cellulose as a binder were weighed at a weight ratio of 97:1:2 and kneaded with water to obtain a negative electrode slurry. The prepared negative electrode slurry was applied to a 15 μm-thick copper foil that is a negative electrode current collector, dried and further pressed, and then a negative electrode was completed.

(Electrolyte Solution)

As a non-aqueous solvent, a mixed solvent of ethylene carbonate, ethyl methyl carbonate and diethyl carbonate (volume ratio: 3:1:6) was used. $LiPF_6$ and hexafluoroglutaric anhydride (FGA) were mixed with this mixed solvent so that the concentration of $LiPF_6$ would be 0.9 mol/l and the concentration of hexafluoroglutaric anhydride would be 0.1 mol/l (1.86 weight %), and an electrolyte solution was prepared.

(Assembly of Secondary Battery)

The prepared positive electrodes and negative electrodes were stacked via a separator to obtain an electrode stack. For the separator, a single-layer polypropylene porous film was used. Here, the number of layers was adjusted so that the initial discharge capacity of the electrode stack would be 100 mAh. Then the current collecting portions of each of the positive electrodes and the negative electrodes were brought together, and an aluminum terminal and a nickel terminal were welded thereto to produce an electrode element. The electrode element was packaged with a laminate film, and the electrolyte solution was injected inside the laminate film. Subsequently, the laminate film was thermally fusion-bonded and sealed while the pressure inside of the laminate film was reduced. Thus, a flat plate type lithium ion secondary battery before initial charge was fabricated. For the laminate film, a polypropylene film on which aluminum was vapor-deposited was used.

(Capacity Retention Rate)

The fabricated flat plate type lithium ion secondary battery was subjected to charge/discharge in the range from 4.2V to 2.5V using a charge/discharge tester (ACD-100M: made by ASKA Electronics Co. Ltd.) in an environment of 45° C. Charge was performed in a CCCV mode at 1 C constant current to 4.2V and at a constant voltage for 1 hour after voltage reaches 4.2V. Discharge was performed in a CC mode at 1 C constant current, and the initial discharge capacity was measured. As used herein, 1 C means a constant current value which is constantly released from a fully charged battery to finish discharge in 1 hour. In this way, 1150 cycles of the charge/discharge were performed, and discharge capacity was respectively measured in pre-determined cycles during this. A ratio (%) of the discharge capacity in each cycle to the initial discharge capacity (in $0^{th}$ cycle) was calculated as a capacity retention rate.

(Impedance Property)

After the fabricated flat plate type lithium ion secondary battery was charged to 4.2 V in a CCCV mode, impedance measurement was carried out in an environment of 25° C. by an alternating impedance method to determine Rsol (solution resistance) and Rct (charge transfer resistance). The impedance measurement was respectively carried out in predetermined cycles in the same manner as the capacity retention rate measurement.

Comparative Example 1

The positive electrode was not coated with the insulating layer. The others were as in Example 1.

Comparative Example 2

Hexafluoroglutaric anhydride was not added to the electrolyte solution. The others were as in Example 1.

Comparative Example 3

The positive electrode was not coated with the insulating layer. Hexafluoroglutaric anhydride was not added to the electrolyte solution. The others were as in Example 1.

Comparative Example 4

Instead of hexafluoroglutaric anhydride, fluoroethylene carbonate (FEC) was added to the electrolyte solution at a concentration of 0.1 mol/l (0.87 weight %), and a battery was produced. The others were as in Example 1.

Comparative Example 5

The positive electrode was not coated with the insulating layer. The others were as in Comparative example 4.

The following Table 1 shows changes in the capacity retention rates of the batteries of Example 1 and Comparative examples 1 to 5.

TABLE 1

| | | Example 1 | Comparative example 1 | Comparative example 2 | Comparative example 3 | Comparative example 4 | Comparative example 5 |
|---|---|---|---|---|---|---|---|
| Insulating layer | | Present | Absent | Present | Absent | Present | Absent |
| Additive | | FGA | FGA | — | — | FEC | FEC |
| Capacity retention rate | 0 | 100.0% | 100.0% | 100.0% | 100.0% | 100.0% | 100.0% |
| | 100 | 92.6% | 95.0% | 94.0% | 96.2% | 93.6% | 95.5% |
| | 250 | 88.4% | 90.7% | 87.8% | 86.8% | 89.0% | 89.0% |
| | 500 | 80.9% | 81.9% | 75.6% | 70.4% | 79.4% | 76.0% |
| | 750 | 74.7% | 74.3% | 64.9% | 57.1% | 72.0% | 64.4% |
| | 1000 | 68.7% | 65.8% | 57.1% | 44.2% | 65.1% | 58.5% |
| | 1150 | 65.3% | 59.1% | 49.0% | 42.4% | 59.4% | 54.9% |

The following Table 2 shows changes in Rsol and Rct of the batteries of Example 1 and Comparative examples 1 to 5.

TABLE 2

| | | Example 1 | Comparative example 1 | Comparative example 2 | Comparative example 3 | Comparative example 4 | Comparative example 5 |
|---|---|---|---|---|---|---|---|
| Insulating layer | | Present | Absent | Present | Absent | Present | Absent |
| Additive | | FGA | FGA | — | — | FEC | FEC |
| Rsol [Ω] | 0 | 0.31 | 0.23 | 0.32 | 0.21 | 0.30 | 0.21 |
| | 100 | 0.34 | 0.30 | 0.33 | 0.25 | 0.35 | 0.25 |
| | 200 | 0.34 | 0.28 | 0.34 | 0.26 | 0.34 | 0.26 |
| | 300 | 0.33 | 0.28 | 0.33 | 0.26 | 0.33 | 0.26 |
| | 400 | 0.35 | 0.29 | 0.34 | 0.26 | 0.34 | 0.27 |
| | 500 | 0.36 | 0.30 | 0.35 | 0.28 | 0.34 | 0.28 |
| | 600 | 0.38 | 0.31 | 0.36 | 0.27 | 0.36 | 0.29 |
| | 700 | 0.37 | 0.31 | 0.37 | 0.28 | 0.35 | 0.28 |
| | 800 | 0.37 | 0.32 | 0.39 | 0.28 | 0.36 | 0.28 |

TABLE 2-continued

|     |      | Example 1 | Comparative example 1 | Comparative example 2 | Comparative example 3 | Comparative example 4 | Comparative example 5 |
|-----|------|-----------|-----------------------|-----------------------|-----------------------|-----------------------|-----------------------|
|     | 1000 | 0.36 | 0.34 | 0.45 | 0.34 | 0.35 | 0.30 |
|     | 1150 | 0.38 | 0.39 | 0.50 | 0.33 | 0.36 | 0.31 |
| Ret | 0    | 0.41 | 0.58 | 0.33 | 0.46 | 0.30 | 0.52 |
| [Ω] | 100  | 1.15 | 0.91 | 1.08 | 0.77 | 1.02 | 0.74 |
|     | 200  | 1.40 | 1.40 | 1.36 | 1.31 | 1.34 | 1.24 |
|     | 300  | 1.52 | 1.48 | 1.71 | 1.50 | 1.44 | 1.27 |
|     | 400  | 1.68 | 1.80 | 2.13 | 2.12 | 2.02 | 1.67 |
|     | 500  | 2.36 | 2.41 | 2.59 | 2.98 | 2.69 | 2.43 |
|     | 600  | 2.55 | 2.69 | 3.30 | 3.75 | 2.94 | 2.85 |
|     | 700  | 2.81 | 3.03 | 3.62 | 4.02 | 3.36 | 3.11 |
|     | 800  | 3.53 | 3.73 | 4.65 | 4.96 | 4.29 | 3.88 |
|     | 1000 | 4.34 | 4.88 | 6.12 | 6.65 | 5.26 | 5.00 |
|     | 1150 | 4.19 | 5.70 | 5.34 | 7.12 | 4.49 | 5.69 |

As shown in Table 1, batteries equipped with the insulating layer tended to have more improved capacity retention rate. Also, in batteries comprising hexafluoroglutaric anhydride, the effect of improving capacity retention rate tended to be large.

As shown in Table 2, an increase in Rsol was distinctly observed in early cycles regardless of additive type when the insulating layer was present. This is because paths for lithium ions to move between the positive electrode and the negative electrode were extended by providing the insulating layer on the positive electrode. When the additive was absent or fluoroethylene carbonate, batteries equipped with the insulating layer had higher Rsol in the $1150^{th}$ cycle in the same manner as in early cycles. However, when the additive was hexafluoroglutaric anhydride, batteries equipped with the insulating layer had lower Rsol in the $1150^{th}$ cycle unlike in early cycles. In the $1150^{th}$ cycle, when the insulating layer was present, Rsol of the battery comprising hexafluoroglutaric anhydride was lower by as much as 0.12Ω than Rsol of the battery not comprising the additive, and the difference thereof to Rsol of the battery comprising fluoroethylene carbonate, which was the smallest, was just 0.02Ω, so they were approximately equal level. In contrast, when the insulating layer was absent, the battery comprising hexafluoroglutaric anhydride had the highest Rsol in the $1150^{th}$ cycle, which was higher by as much as 0.06Ω than the battery not comprising the additive. The same applies to Rct, and, the combination of the insulating layer and hexafluoroglutaric anhydride resulted in the lowest Rct in the $1150^{th}$ cycle.

Batteries comprising hexafluoroglutaric anhydride are improved in life characteristics, but have the problem of the big increase in Rsol. However, these results show that the insulating layer on a positive electrode further improves life characteristics thereof and largely reduces the increase in Rsol caused by adding hexafluoroglutaric anhydride, and thereby a battery having a small increase in resistance can be obtained.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

INDUSTRIAL APPLICABILITY

The lithium ion secondary battery according to the present embodiment can be utilized in, for example, all the industrial fields requiring a power supply and the industrial fields pertaining to the transportation, storage and supply of electric energy. Specifically, it can be used in, for example, power supplies for mobile equipment such as cellular phones and notebook personal computers; power supplies for electrically driven vehicles including an electric vehicle, a hybrid vehicle, an electric motorbike and an electric-assisted bike, and moving/transporting media such as trains, satellites and submarines; backup power supplies for UPSs; and electricity storage facilities for storing electric power generated by photovoltaic power generation, wind power generation and the like.

EXPLANATION OF SYMBOLS

10 film outer package
20 battery element
25 separator
30 positive electrode
40 negative electrode

The invention claimed is:
1. A lithium ion secondary battery, comprising:
a positive electrode comprising:
a positive electrode current collector,
a positive electrode active material layer formed on the positive electrode current collector, and
a porous layer comprising aluminum oxide and polyvinylidene fluoride (PVdF) formed on the positive electrode active material layer,
a negative electrode comprising graphite, and
an electrolyte solution,
wherein the porous layer comprising the aluminum oxide and the PVdF is formed by applying a coating material for forming the porous layer directly on the positive electrode,
the positive electrode active material layer comprises a positive electrode active material represented by the following formula (3):

$$LiNi_{62}Co_{\gamma}Mn_{\delta}O_2 \qquad (3),$$ 

wherein, in formula (3), 0.75≤β≤0.85, 0.05γ≤0.15, 0.10≤δ≤0.20, and β+γ+δ=1; and
the electrolyte solution comprises:
0.05 to 5 weight % of hexafluoroglutaric anhydride, and,
a non-aqueous solvent comprising ethylene carbonate (EC), diethyl carbonate (DEC), and ethyl methyl carbonate (EMC).
2. A vehicle equipped with the lithium ion secondary battery according to claim 1.
3. A method for manufacturing a lithium ion secondary battery comprising a positive electrode, a separator, a negative electrode, and an electrolyte solution, the negative electrode comprising graphite, the positive electrode comprising a positive electrode current collector, a positive electrode active material layer, and a porous layer comprising aluminum oxide and polyvinylidene fluoride (PVdF) formed on the positive electrode active material layer, the method comprising the steps of:

fabricating an electrode element by stacking the positive electrode and the negative electrode via the separator, and enclosing the electrode element and the electrolyte solution into an outer package, wherein the electrolyte solution comprises 0.05 to 5 weight % of a hexafluoroglutaric anhydride, and a non-aqueous solvent comprising ethylene carbonate (EC), diethyl carbonate (DEC), and ethyl methyl carbonate (EMC), the positive electrode active material layer comprises a positive electrode active material represented by the following formula (3):

$$LiNi_{\beta}Co_{\gamma}Mn_{\delta}O_2 \tag{3}$$

wherein, in formula (3), $0.75 \leq \beta \leq 0.85$, $0.05 \gamma \leq 0.15$, $0.10 \leq \delta \leq 0.20$, and $\beta+\gamma+\delta=1$; and the porous layer comprising the aluminum oxide and PVdF is formed by applying a coating material for forming the porous layer directly on the positive electrode.

* * * * *